United States Patent [19]

Szabo et al.

[11] Patent Number: 4,485,260
[45] Date of Patent: Nov. 27, 1984

[54] PREPARATION OF UNSYMMETRICAL DIPHENYLAMINES

[75] Inventors: Paul Szabo, Islington; Daniel E. Freeman, Mississauga; Trevor I. Martin, Burlington; John M. Lennon, Mississauga, all of Canada

[73] Assignee: Xerox Corporation, Stamford, Conn.

[21] Appl. No.: 360,263

[22] Filed: Mar. 22, 1982

Related U.S. Application Data

[63] Continuation of Ser. No. 81,308, Oct. 3, 1979, abandoned.

[51] Int. Cl.³ .................. C07C 91/44; C07C 85/06
[52] U.S. Cl. .................................... 564/402; 564/403
[58] Field of Search ............................. 564/402, 403

[56] References Cited

U.S. PATENT DOCUMENTS

| | | | |
|---|---|---|---|
| 1,885,355 | 11/1932 | Jones | 564/402 |
| 2,000,410 | 5/1935 | Morrell et al. | 564/402 X |
| 2,013,052 | 9/1935 | Horsley | 564/402 |
| 3,170,956 | 2/1965 | Olin | 564/402 |

FOREIGN PATENT DOCUMENTS

| | | | |
|---|---|---|---|
| 1358816 | 9/1974 | United Kingdom | 564/402 |
| 1486641 | 9/1977 | United Kingdom | 564/402 |

Primary Examiner—Thomas A. Waltz
Attorney, Agent, or Firm—Peter H. Kondo; John E. Beck; Ronald Zibelli

[57] ABSTRACT

There is disclosed a process for the production of unsymmetrical, substituted diarylamines by the reaction of a primary aromatic amine and a substituted phenol wherein the phenol is held in excess of the primary aromatic amine thereby minimizing by-product formation as a result of self-condensation of the primary arylamine. The desired secondary amine is produced in high yield and purity by recycling the unreacted phenol.

10 Claims, 1 Drawing Figure

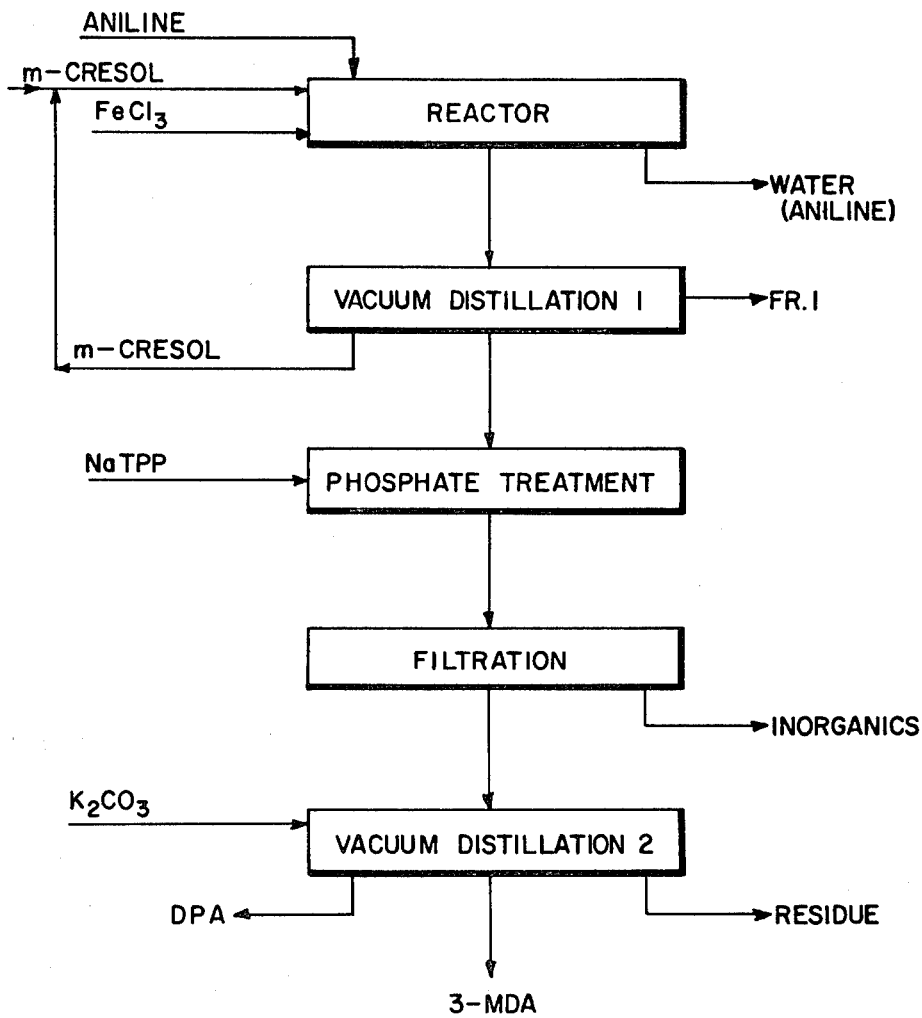

PREPARATION OF UNSYMMETRICAL DIPHENYLAMINES

This application is a continuation-in-part of copending application U.S. Ser. No. 081,308, filed Oct. 3, 1979, now abandoned, in the names of Paul Szabo, Daniel E. Freeman, Trevor I. Martin and John M. Lennon. Copending application U.S. Ser. No. 081,308 is incorporated herein in its entirety.

BACKGROUND OF THE INVENTION

This invention relates to the preparation of unsymmetrical, substituted diphenylamines and a particular 3-methyldiphenylamine.

There has long been known procedures for the production of symmetrical, unsubstituted diphenylamines. Aniline is normally condensed in the vapor phase in the presence of a catalyst. Such processes are disclosed in U.S. Pat. Nos. 3,079,439 and 3,118,944. The production of diphenylamine from aniline in the liquid phase is disclosed in U.S. Pat. No. 3,205,265 wherein the reaction is catalyzed by a halogen and an oxygen containing compound of phosphorous.

It has also been disclosed in U.S. Pat. No. 1,885,355 that a symmetrical unsubstituted diamine such as di-beta-naphthol p-phenylenediamine could be prepared by reacting a diamine such as p-phenylenediamine with an excess of a substituted fused benzene ring reactant such as beta-naphthol.

More recently, there has been disclosed a process for the manufacture of diarylamines by the reaction of a phenol and aniline in the presence of a small concentration of sulfonic acid. Such process is disclosed in German Pat. No. 2,042,774. This patent suggests the manufacture of both symmetrical and unsymmetrical substituted diphenylamines in the presence of the acid catalyst. A continuous process is suggested through the use of interconnected autoclaves in succession whereby each autoclave is outfitted with a distillation column for the removal of water produced in the reaction. According to this process, the reaction operates with an excess of aniline. Under these conditions, the self-condensation of aniline leads to the formation of a substantial amount of by-product which is diphenylamine.

In yet another process described in Canadian Pat. No. 1,005,462, there is described a process for the production of diarylamines by the reaction of naphthol and a primary arylamine. In such process, ferric chloride is utilized as a catalyst. As in similar prior art, the primary arylamine is utilized in excess and therefore the formation of by-product by self-condensation of the primary arylamine is significant.

Generally, there is in the prior art relating to unsymmetrical, substituted diphenylamines a great tolerance for impurities in the final product, usually diphenylamine resulting from the self-condensation of aniline. The presence of such an impurity was probably of little concern because the end use of the product did not require high purity. However, there is a need to provide unsymmetrical, substituted diarylamines in high yield and purity when such amines are utilized as precursors for other products.

SUMMARY OF THE INVENTION

In accordance with the present invention, there is provided a process for the production of unsymmetrical, substituted diarylamines by the reaction of a primary arylamine and a substituted phenolic compound wherein the phenolic compound is present in excess of the amine. Subsequent to completion of the reaction, the unreacted phenolic compound is recovered and recycled for reaction with additional primary arylamine. Surprisingly, the process provides for the suppression of the self-condensation of the primary arylamine while still providing for a high yield of the desired unsymmetrical substituted diarylamine.

DETAILED DESCRIPTION OF THE INVENTION

The process of this invention successfully achieves suppression of the traditional problem of self-condensation of primary arylamines by employing an excess of the phenolic compound in the reaction mixture. Generally, the molar ratio of primary arylamine to the phenolic compound is in the range of from about 0.1:1 to about 0.7:1. However, a molar ratio of primary arylamine to phenolic compound of about 0.3:1 has been found to be optimum. The excess phenolic compound is subsequently recovered easily from the reaction mixture for reuse in subsequent production of the desired substituted, unsymmetrical diarylamine. By the recycling step, a high yield and overall conversion is achieved even though low conversion is experienced in each individual reaction. A catalyst has been found to be necessary in the process of this invention to increase the rate of reaction between the phenolic compound and the primary amine. Any suitable catalyst can be employed, preferably ferric chloride. Other catalysts include benzenesulfonic acid, toluenesulfonic acid, sulfuric acid, and acidic alumina. The amount of catalyst utilized is usually in the range of from about 1 to about 15 percent by weight of both reactants, although about 5 percent by weight has been found to be most efficient.

Various substituted or unsubstituted primary arylamines can be employed in the process of this invention. These primary arylamines have the general formula

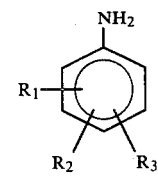

wherein $R_1$, $R_2$ and $R_3$ represent hydrogen, methyl, ethyl, n-propyl, iso-propyl, n-butyl, sec-butyl, tert-butyl, phenyl and alkyl substituted phenyl. $R_1$, $R_2$ and $R_3$ may be the same group or different groups. Typical substituted arylamines include aniline, ortho-toluidine, meta-toluidine, para-toluidine, 4-amino-3'-methylbiphenyl, 2,3-dimethylaniline, 2,4-dimethylaniline, 3,5-dimethylaniline, ethyl-2-methylaniline, 2,3,4-trimethylaniline, 2,3-dimethyl-5-ethylaniline and the like. For the particular case of 3-methyldiphenylamine, aniline is preferred because of its availability and low cost.

The substituted phenolic compounds of most interest are mono-, di- or tri-substituted phenols having the general formula

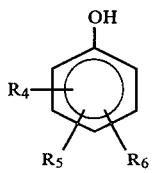

wherein

R$_4$ represents methyl, ethyl, n-propyl, iso-propyl, n-butyl, sec-butyl, tert-butyl, phenyl and substituted phenyl, the substituted phenyl having attached to the benzene ring an alkyl, phenyl or hydroxy group;

R$_5$ and R$_6$ represent hydrogen, hydroxy, methyl, ethyl, n-propyl, iso-propyl, n-butyl, sec-butyl, tert-butyl, phenyl and substituted phenyl, the substituted phenyl having attached to the benzene ring an alkyl, phenyl or hydroxy group; and R$_5$ and R$_6$ may be the same groups or different groups.

Typical phenolic compounds include ortho-cresol, meta-cresol, para-cresol, 2,3 dimethylphenol, 2,4 dimethylphenol, 2,5 dimethylphenol, 2,6 dimethylphenol, 3,5 dimethylphenol, 3,4 dimethylphenol, catechol, hydroquinone, resorcinol, p,p-biphenol, o,o-biphenol, o-hydroxy biphenyl, trimethylphenol, dimethyl ethyl phenol, and the like. For the particular case of 3-methyldiphenylamine, m-cresol is preferred.

The reaction of the primary arylamine and the substituted phenol to form the unsymmetrical, substituted diarylamine is illustrated below:

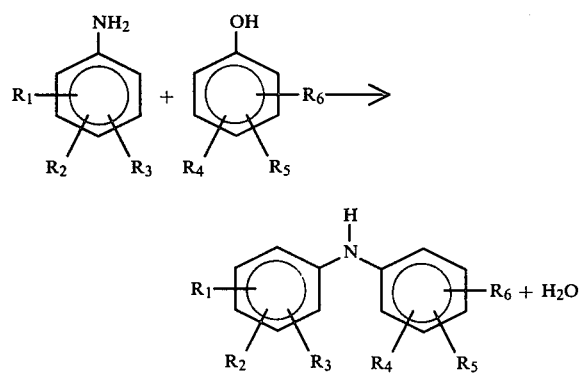

where R$_1$, R$_2$, R$_3$, R$_4$, R$_5$ and R$_6$ are defined above.

The reaction should be conducted under sufficient elevated pressure to prevent loss of the reactants. Reactants boil off at atmospheric pressure under reaction temperatures. Satisfactory results may be achieved with pressures between about 150 pounds per square inch and about 250 pounds per square inch if the water is continuously vented from the reaction vessel. Pressures up to about 700 pounds per square inch may be employed for closed reaction vessels.

Reaction temperatures of between about 200° C. and about 400° C. are satisfactory. The reaction rate below about 200° C. is undesirably slow. Temperatures about 400° C. severely tax the reactors. Temperatures between about 280° C. and about 350° C. are preferred for greater reaction rates. Optimum results are achieved with reaction temperatures between about 300° C. and about 330° C.

BRIEF DESCRIPTION OF THE DRAWING

FIG. 1 provides a flow chart outlining the various steps in the process of this invention.

DETAILED DESCRIPTION OF THE DRAWING

A typical reaction involves aniline and m-cresol with ferric chloride as the catalyst. Accordingly, in FIG. 1, a pressure reactor system equipped with a stirrer is charged with about 5 moles of aniline, 16.6 moles of m-cresol and about 0.71 moles of anhydrous ferric chloride. The reaction is typically operated under an inert atmosphere of nitrogen at a temperature in the range of about 280° C. to 350° C. Since water is produced during the reaction, a control valve is utilized to periodically vent the system allowing water to be removed during the reaction as it accumulates. The reaction proceeds for about 20 minutes to about 9 hours and more preferably between about 1 hour to about 6 hours depending on the operating temperature. As the reaction proceeds, the pressure oscillates in the narrow range of the control valve setting as water is removed, but is maintained between about 150 psi and about 250 psi. If desired, the water may be removed continuously rather than periodically. A small amount of aniline escapes with the water but is inconsequential and can be easily recovered. At the end of the reaction, the reactor is cooled and the entire contents of the reactor are transferred to a vacuum distillation system. The catalyst could be removed by filtration prior to distillation. The first fraction, as indicated in FIG. 1 by Fr. 1, is removed and contains water with traces of m-cresol and aniline. This is discarded and a second fraction is obtained containing about 98 percent m-cresol with traces of aniline, diphenylamine and 3-methyldiphenylamine. This fraction is reused as the m-cresol for the next batch as indicated in FIG. 1.

The residue from the vacuum distillation is then treated with a phosphate to remove traces of iron from the product. In this illustrative procedure, about 0.1 parts by weight of sodium tripolyphosphate is added to 1 part residue. The mixture is held at about 100° C. for about one hour with stirring. This mixture is then filtered to remove the inorganic salts as indicated in FIG. 1 with the filtrate being transferred to a vacuum distillation system. Only if traces of iron are detrimental to the quality of the final product, the residue may be treated with phosphate. It has been found that a small amount of potassium carbonate added to this second distillation results in the production of a colorless product. An intermediate fraction is obtained containing traces of m-cresol, aniline, diphenylamine and a slight amount of 3-methyldiphenylamine. This is indicated in FIG. 1 as "DPA" and may be combined with subsequent batches for recovery of the useful material therein. The main fraction is recovered at a temperature in the range of from about 170° C. to about 180° C. under $10^{-2}$ mm of mercury vacuum to provide 3-methyldiphenylamine in excess of 97 percent purity. A small amount of diphenylamine is also present. The diphenylamine content of the final product is dependent upon the efficiency of the distillation unit. The residue is easily removed from the distillation system.

As indicated above, the excess phenolic compound is recycled thereby providing a high yield and overall conversion while at the same time providing a highly pure product.

The foregoing process is repeated with about 5 moles of aniline, about 8.3 moles of m-cresol and about 0.45 moles of anhydrous ferric chloride. The resulting product comprises about 92 percent by weight 3-methyldiphenyl amine and about 8 percent by weight diphenylamine as opposed to the reaction described above which gave a product containing 97 percent by weight 3-methyl diphenylamine and 3 percent by weight diphenylamine. This clearly illustrates that the degree of self-condensation of aniline is dramatically affected by the ratio of primary aromatic amine and substituted phenol employed.

The foregoing process is repeated with about 5 moles of aniline, about 16.6 moles of m-cresol and no catalyst. No significant amount of 3-methyldiphenylamine could be detected by liquid and gas chromatography at the end of the reaction. This clearly demonstrates that this reaction will not proceed in the absence of a catalyst.

Since the reactants will boil away at temperatures above their boiling points and since the reaction must be effected at temperatures above the boiling points of the reactants, the reaction cannot be successfully conducted at atmospheric pressure.

Paul C. Jones, discloses in U.S. Pat. No. 1,885,355 a process for preparing a symmetrical secondary aromatic amine at 300° C. in the absence of a catalyst. In an example in line 73, page 1 through line 2, page 2 of the Jones patent, 400 pounds of 2-naphthol and 100 pounds of p-phenylenediamine are reacted at 300° C. for a period of 2 hours to form a crude containing 2-naphthol and N,N'-di-beta naphthyl p-phenylenediamine. This crude is comminuted into a fine powder and washed with 115 gallons of hot denatured alcohol followed by 25 gallons of cold alcohol to yield a pure product of 98 percent yield. These conditions were reproduced using 20 grams of p-phenylenediamine and 80 grams of 2-naphthol in an open stainless steel reactor equiped with a condenser. The reactor was electrically heated to 300° C. and maintained at that temperature 2 hours. A second run using 20 grams of p-phenylenediamine and 57 grams of 2-naphthol is carried out under identical reaction conditions and procedures. Both product cakes, following comminution, were slurried in 500 ml of absolute methanol and refluxed for three hours. The slurry was then filtered while hot and the resulting product cake rinsed with fresh cold methanol. After the product was dried, liquid chromatographic analysis was accomplished on each product, and substantially identical results were achieved with both reactions. This clearly demonstrates that self-condensation of the p-phenylenediamine does not take place in the reaction and that the mole ratio does not affect self-condensation of the diamine.

Other modifications and ramifications of the present invention will occur to those skilled in the art upon a reading of the present disclosure. These are intended to be included within the scope of this invention.

We claim:

1. A process for the preparation of a substituted, unsymmetrical diphenylamine comprising reacting a primary arylamine having the general formula:

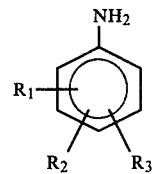

wherein $R_1$, $R_2$ and $R_3$ are selected from the group consisting of hydrogen, methyl, ethyl, n-propyl, iso-propyl, n-butyl, sec-butyl, tert-butyl, phenyl and alkyl substituted phenyl, and a substituted phenol having the general formula:

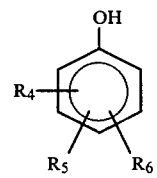

wherein $R_4$ is selected from the group consisting of methyl, ethyl, n-propyl, iso-propyl, n-butyl, sec-butyl, tert butyl, phenyl and substituted phenyl, said substituted phenyl having attached to the benzene ring an alkyl, phenyl or hydroxy group and $R_5$ and $R_6$ are selected from the group consisting of hydrogen, hydroxy, methyl, ethyl, n-propyl, iso-propyl, n-butyl, sec-butyl, tert-butyl, phenyl and substituted phenyl, the substituted phenyl having attached to the benzene ring an alkyl, phenyl or hydroxy group in the presence of a catalyst by heating at an elevated pressure and maintaining the alkyl substituted phenol in excess of the primary arylamine whereby self-condensation of the substituted amine is supressed.

2. The process of claim 1 wherein the primary arylamine is aniline and the alkyl substituted phenolic compound is m-cresol.

3. The process of claim 2 wherein the catalyst is ferric chloride.

4. The process of claim 3 wherein the molar ratio of aniline to cresol is in the range of from about 0.1:1 to about 0.7:1.

5. The process of claim 4 wherein the excess cresol is recovered from the reaction product and recycled to said process.

6. The process of claim 5 wherein the molar ratio of aniline to cresol is about 0.3:1.

7. The proceess of claim 1 wherein the pressure is maintained at an elevated pressure up to about 700 psi.

8. The process of claim 1 wherein water produced during the reaction is continuously removed by venting through a pressure sensitive control valve.

9. The process of claim 8 wherein the pressure during the reaction is maintained between about 150 psi and about 250 psi.

10. The process of claim 1 wherein the reaction is conducted at between about 280° C. and about 350° C.

* * * * *